(12) United States Patent
Sundermeier et al.

(10) Patent No.: US 8,030,520 B2
(45) Date of Patent: Oct. 4, 2011

(54) PROCESS FOR PREPARING ORGANIC COMPOUNDS BY A TRANSITION METAL-CATALYSED CROSS-COUPLING REACTION OF AN ARYL-X, HETEROARYL-X, CYCLOALKENYL-X OR ALKENYL-X COMPOUND WITH AN ALKYL, ALKENYL, CYCLOALKYL OR CYCLOALKENYL HALIDE

(75) Inventors: Mark Sundermeier, Düsseldorf (DE); Matthias Gotta, Köln (DE); Axel Jacobi von Wangelin, Köln (DE); Waldemar Maximilian Czaplik, Burscheid (DE)

(73) Assignee: Saltigo GmbH, Langenfeld (DE)

( * ) Notice: Subject to any disclaimer, the term of this patent is extended or adjusted under 35 U.S.C. 154(b) by 0 days.

(21) Appl. No.: 12/407,947

(22) Filed: Mar. 20, 2009

(65) Prior Publication Data

US 2009/0247764 A1 Oct. 1, 2009

(30) Foreign Application Priority Data

Mar. 31, 2008 (DE) .......................... 10 2008 016 702
Dec. 17, 2008 (DE) .......................... 10 2008 062 690

(51) Int. Cl.
*C07C 211/00* (2006.01)
(52) U.S. Cl. ........................................................ 564/305
(58) Field of Classification Search .................... 564/305
See application file for complete search history.

(56) References Cited

U.S. PATENT DOCUMENTS

2003/0220498 A1 11/2003 Furstner et al. ............... 544/179

FOREIGN PATENT DOCUMENTS

EP 1724248 11/2006

OTHER PUBLICATIONS

"Iron-Catalyzed Alkylations of Aromatic Grignard Reagents", Cahiez et. al., Angew. Chem. Int. Ed. 2007, 46, 4364-4366.*
Czaplik et. al., "Domino Iron Catalysis: Direct Aryl-Alkyl Cross Coupling", Angewandte Chem. Int. Ed. , 48, pp. 607-610 , 2009, published online Sep. 8, 2008.*
Dohle et. al., "Fe (III)-Catalyzed Cross-Coupling Between Functionalized Arylmagnesium Compounds and Alkenyl Halides", Synlett 2001, No. 12, pp. 1901-1904.*
Kochi et al., J. Am. Chem. Soc. (1971), 1487.
Fürstner, Chem. Lett. (2005), 624.
Fürstner, Angew. Chem.(2002), 632.
Nakamura, J. Am. Chem. Soc. (2004), 3686.
Knochel, Synlett (2001), 1901.
Cahiez, Angew. Chem. Int. Ed. (2007), 4364.
Angew. Chem. (2005), 3007.
Knochel, Tetrahedron Lett. (1998), 6163.
Tetrahedron (2006). 2207.
Hayashi, Chem. Comm. (2007), 4513.
Von Wangelin, et al., Angew. Chem. Inc. (2009), 48, 607-610.
Oshima, J. Am. Chem. Soc. (2006), 1886.
Cahiez, Tetrahedron Lett. (1998), 6159.
European Search Report from co-pending Application EP09155811 dated Aug. 20, 2009.

* cited by examiner

*Primary Examiner* — Janet Andres
*Assistant Examiner* — Heidi Reese
(74) *Attorney, Agent, or Firm* — Michael A. Miller

(57) ABSTRACT

This invention relates to a process for preparing functionalized aryl, heteroaryl, cycloalkenyl, or alkenyl compounds, by a transition-metal-catalyzed cross-coupling reaction of a substituted or unsubstituted aryl-X, heteroaryl-X, cycloalkenyl-X or alkenyl-X compound with an alkyl, alkenyl, cycloalkyl or cycloalkenyl halide, where X is a halide, diazonium, tosylate (p-toluenesulphonate), mesylate (methanesulphonate) or triflate (trifluoromethanesulphonate) leaving group.

4 Claims, No Drawings

PROCESS FOR PREPARING ORGANIC COMPOUNDS BY A TRANSITION METAL-CATALYSED CROSS-COUPLING REACTION OF AN ARYL-X, HETEROARYL-X, CYCLOALKENYL-X OR ALKENYL-X COMPOUND WITH AN ALKYL, ALKENYL, CYCLOALKYL OR CYCLOALKENYL HALIDE

The invention relates to a process for preparing organic compounds, in particular functionalized aryl, heteroaryl, cycloalkenyl or alkenyl compounds, by a transition metal-catalysed cross-coupling reaction of a substituted or unsubstituted aryl-X, heteroaryl-X, cycloalkenyl-X or alkenyl-X compound with an alkyl, alkenyl, cycloalkyl or cycloalkenyl halide, where X is a halide, diazonium, tosylate (p-toluenesulphonate), mesylate (methanesulphonate) or triflate (trifluoromethanesulphonate) leaving group.

Transition metal-catalysed cross-couplings are among the most important synthetic tools in modern organic chemistry. Palladium and nickel catalysts in particular are widely used here, including in industrial synthesis. Thus, for example, palladium-catalysed Suzuki-Miyaura cross-couplings are used for the synthesis of various pharmacologically active substances. The synthesis of functionalized styrenes, for example 4-chlorostyrene, is an industrially established cross-coupling based on nickel catalysts.

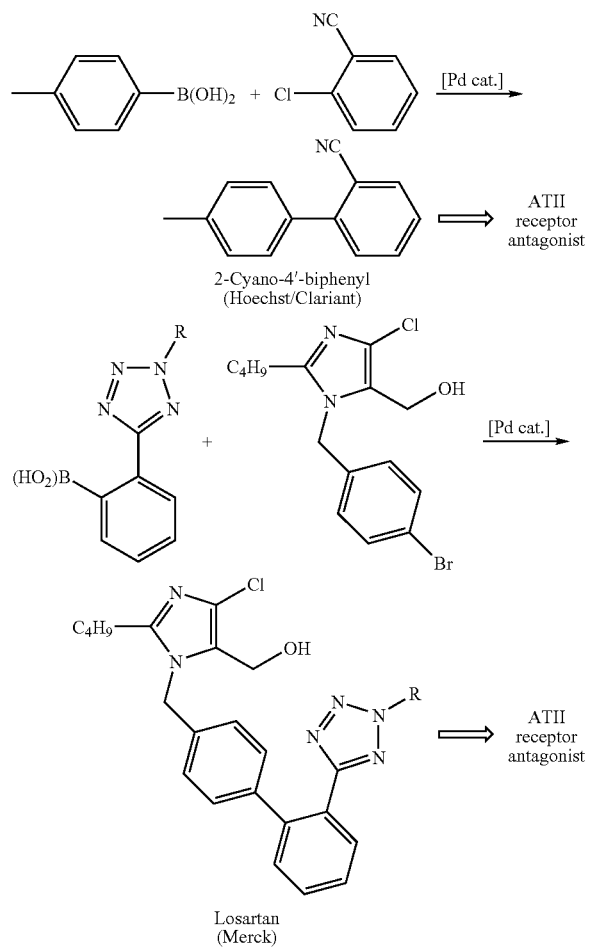

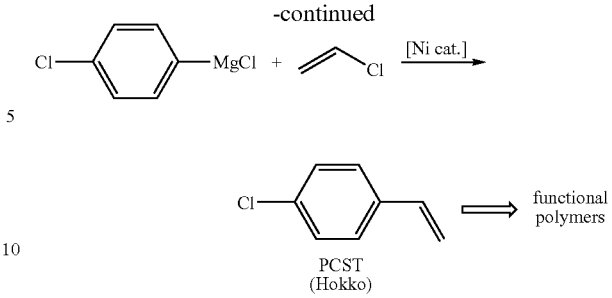

For economic reasons (high world market prices for palladium) and toxicological reasons (high toxicity of nickel and palladium compounds), the use of the two metals as catalysts in industry suffers from significant disadvantages. Furthermore, the world market prices for metals such as palladium or nickel are expected to display great increases in the future and will continue to restrict industrial use in syntheses. Increasing efforts are therefore being made to find other, catalytically active systems which employ advantageous, readily available and nontoxic metals.

Apart from nickel and palladium compounds, iron and cobalt compounds also display activity in cross-coupling reactions under particular reaction conditions.

Iron is, for economic and toxicological reasons, far superior to the nickel and palladium compounds. Iron is estimated to be the tenth most abundant element in the universe, and 5% of the earth's crust consists of iron. Owing to the ease of mining it and the ease of isolating it from ores, many different iron compounds can be obtained inexpensively in large quantities. Likewise, various cobalt salts can be obtained cheaply and are therefore preferred to, for example, palladium as catalyst systems.

Kochi et al. showed as early as the beginning of the 1970s that iron salts can catalyse the cross coupling of vinyl halides with alkyl Grignard compounds (Kochi et al., J. Am. Chem. Soc. (1971), 1487).

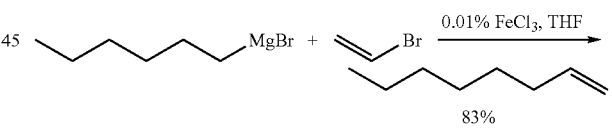

Owing to the narrow substrate spectrum and therefore a rather small range of uses of the method, it attracted little interest. Over 30 years later, other studies by Knochel, Fürstner, Cahiez and Nakamura optimized the iron-catalysed cross-coupling by use of nitrogen-containing additives such as N-methyl-2-pyrrolidone (NMP) or N,N,N',N'-tetramethylethylenediamine (TMEDA) and thus drew it to the attention of current researchers.

The mild reaction conditions (from −20° C. to 35° C.), the short reaction times (generally less than 60 minutes) and the broad substrate spectrum make iron-catalysed cross-coupling extremely interesting as a synthetic tool.

Fürstner et al. synthesized a number of natural materials (including FTY720 and (R)-(+)-muscopyridine) using iron-catalysed cross-couplings (Fürstner, Chem. Lett. (2005), 624).

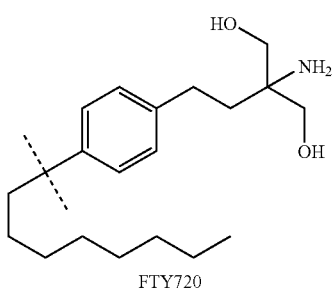

FTY720

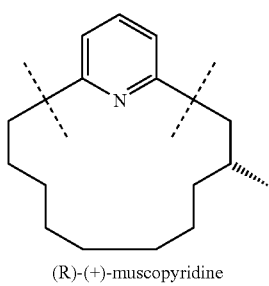

(R)-(+)-muscopyridine

FTY720 and (R)-muscopyridine.

According to Fürstner et al., a covalent iron-magnesium cluster of the formal composition Fe(MgX)$_2$ is responsible for the catalytic activity. In this cluster, the iron atom has the formal oxidation number minus two (superferrate cluster).

Furthermore, Fürstner et al. developed a method for the cross-coupling of functionalized aryl chlorides and triflates with alkylmagnesium compounds in the presence of 5 mol % of iron(III) acetylacetonate and a THF/NMP solvent mixture as catalyst system (Fürstner, Angew. Chem. (2002), 632).

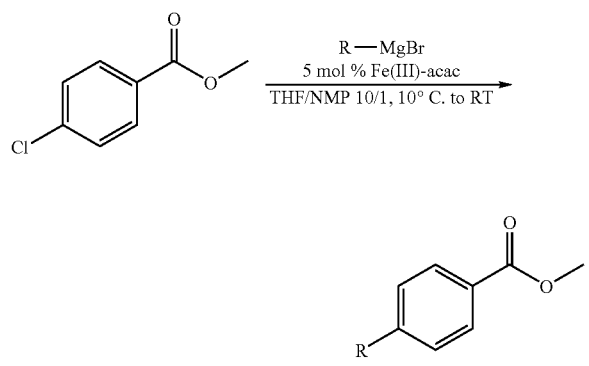

R=hexyl (95), isopropyl (59), 6-hexenyl (91), phenyl (28)

Yields in parentheses (GC, %)

This method allows the use of esters, amines and chlorinated heteroaromatics and thus makes wider use in the synthesis of natural materials possible.

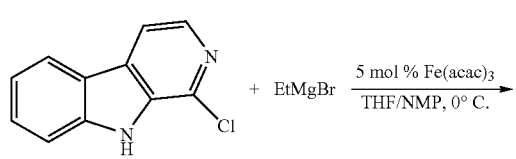

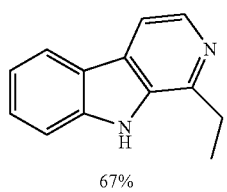

67%

In 2004, Nakamura et al. developed a cross-coupling of alkyl halides with arylmagnesium compounds using 5 mol % of iron(III) chloride and TMEDA (N,N,N',N'-tetramethylethylenediamine) as additive (Nakamura, J. Am. Chem. Soc. (2004), 3686).

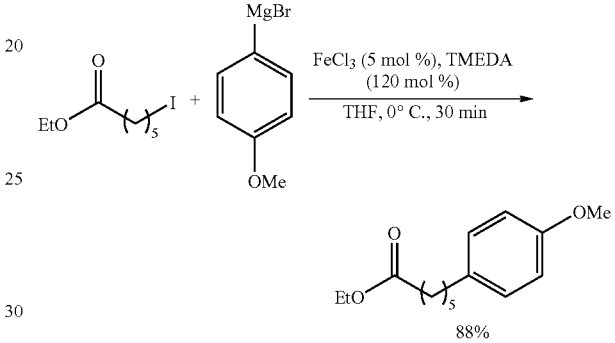

In 2001, Knochel et al. published a cross-coupling of highly functionalized arylmagnesium compounds which had previously been formed by means of a transmetallation step. These can be converted in a further transmetallation into more stable copper organyls or be used directly in a cross-coupling with vinyl bromides or iodides at a lower temperature (Knochel, Synlett (2001), 1901).

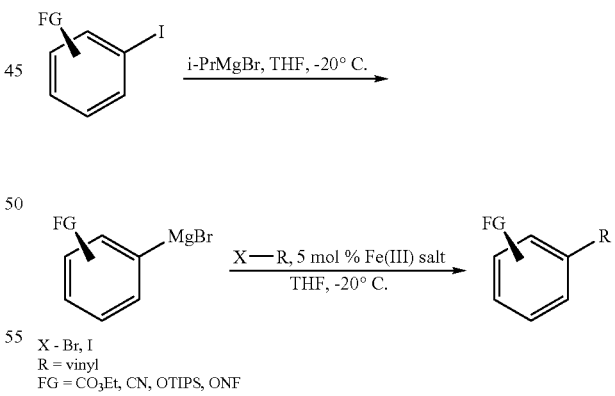

X = Br, I
R = vinyl
FG = CO$_2$Et, CN, OTIPS, ONF

In 2007, Cahiez et al. developed an efficient iron-catalysed cross-coupling using catalytic amounts of TMEDA (N,N,N',N'-tetramethylethylenediamine) (10 mol %) and hexamethylenetetramine (5 mol %). This method is especially suitable for the coupling of aryl Grignard compounds with secondary and primary halides. Secondary halides generally give better yields of coupling product (Cahiez, Angew. Chem. Int. Ed. (2007), 4364).

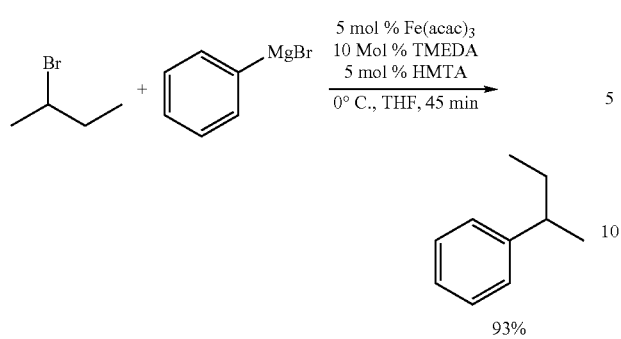

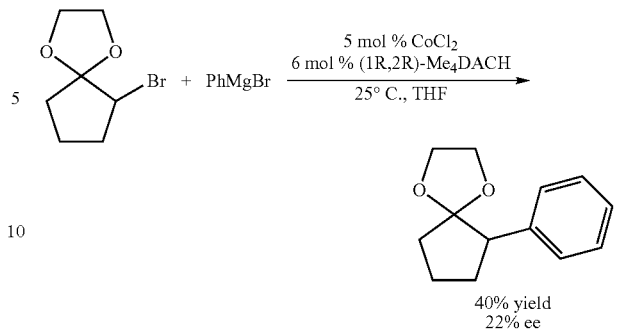

Use of a nonhygroscopic (FeCl₃)₂(TMEDA)₃ complex enabled the amount of catalyst to be reduced to 1.5 mol %. The complex, which is easy to prepare and store, makes a very simple but efficient cross-coupling possible.

In 2007, Hayashi et al. were able to show that not only alkyl, alkenyl and aryl Grignard compounds but also alkynyl Grignard compounds can be used in the cobalt-catalysed cross-coupling with alkenyl triflates (Hayashi, Chem. Comm. (2007), 4513).

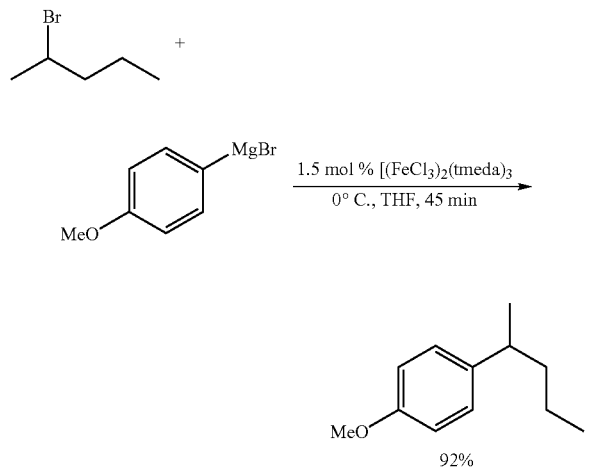

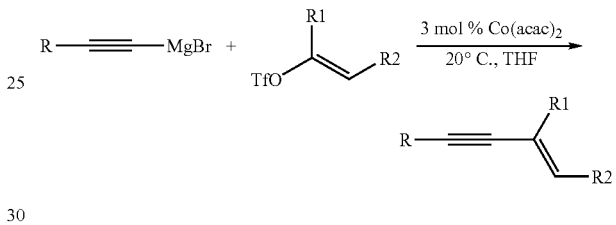

The first efficient cobalt-catalysed cross-couplings of alkenyl halides with alkyl Grignard compounds were published by Cahiez et al. at the end of the 1990s. CoCl₂ and Co(acac)₂ in an NMP/THF solvent mixture served as catalyst system (Cahiez, Tetrahedron Lett. (1998), 6159).

The abovementioned iron- and cobalt-catalysed cross-couplings are all based on the coupling of an organomagnesium compound (Grignard compound) with an alkyl, alkenyl or aryl halide.

The Grignard compound has to be prepared separately beforehand and, as, for example, in the method of Nakamura et al., be slowly added dropwise over a relatively long period of time (Nakamura, J. Am. Soc. (2004), 3686). Particularly on a relatively large scale, the storage of pyrophoric Grignard compounds is problematical and handling them is difficult because of their sensitivity to atmospheric moisture. This hazard potential makes it necessary to observe particular measures in terms of process safety when they are used in industry, which makes implementation on a large scale significantly more difficult.

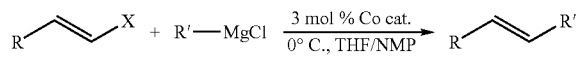

Knochel et al. extended this cobalt-catalysed cross-coupling method to the reaction of alkenyl and aryl halides with organocopper and organozinc compounds (Knochel, Tetrahedron Lett. (1998), 6163; Angew. Chem. (2005), 3007).

The first stereoselective variant displaying moderate selectivities in the cobalt-catalysed cross-coupling of an alkyl halide with an aryl Grignard compound was described in 2006 by Oshima et al. The influence of an adjacent centre of chirality on the alkyl halide on the diastereoselectivity of the cross-coupling was also examined. Furthermore, it was shown that not only amines but also diphosphines are suitable as ligands in the cobalt-catalysed cross-coupling of alkyl halides with aryl Grignard compounds (Oshima, J. Am. Chem. Soc. (2006), 1886; Tetrahedron (2006). 2207).

It was therefore an object of the present invention to discover a process for preparing organic compounds in which it is not necessary for an organomagnesium compound (Grignard compound) to be prepared and isolated separately.

A process which combines a transition metal-catalysed formation of a Grignard compound with a direct cross-coupling with an organic halide in a one-pot reaction has now been found. The hazards associated with the storage and separate preparation of organomagnesium compounds are therefore not present in the process of the invention. Furthermore, utilization of only one reaction vessel enables the efficiency and utilization of space to be increased significantly in the process of the invention compared to conventional processes.

The invention accordingly provides a process for preparing organic compounds of the general formula (I)

R—R'    (I), where
R is a substituted or unsubstituted aromatic, heteroaromatic, cycloalkenylic or alkenylic radical and
R' is a substituted or unsubstituted alkylic, alkenylic, cycloalkylic or cycloalkenylic radical, by reacting a corresponding compound of the general formula (II)

$$R\text{---}X \quad (II),$$

where
X is chlorine, bromine, iodine, diazonium, mesylate (methanesulphonate), tosylate (p-toluenesulphonate) or triflate (trifluoromethanesulphonate) and
R is as defined for formula (I),
with a corresponding compound of the general formula (III)

$$R'\text{---}Y \quad (III),$$

where
Y is chlorine, bromine or iodine and
R' is as defined for formula (I),
wherein the reaction is carried out in the presence of
a) stoichiometric amounts of elemental magnesium, based on the compound of the general formula (II), and
b) catalytic amounts of a transition metal compound, based on the compound of the general formula (II),
and, if appropriate,
c) in the presence of a nitrogen-, oxygen- and/or phosphorus-containing additive in a catalytic or stoichiometric amount, based on the compound of the general formula (II).

It is particularly advantageous that the process of the invention is carried out as a one-pot process and the organomagnesium compound (Grignard compound) formed in situ as intermediate is not isolated.

The transition metal compounds, in particular the iron and cobalt compounds mentioned, catalyse the formation of organomagnesium compounds from halides at low temperatures. The Grignard compounds formed in this way are, according to the invention, directly reacted further in situ with an aryl-X compound, heteroaryl-X compound or alkenyl-X compound in a cross-coupling reaction using the same catalytic system. The group X in formula (II) is a leaving group which can be a halide, diazonium, mesylate, tosylate or triflate. The concentration of active Grignard compound remains very low because of the rapid subsequent reaction. Experiments have confirmed that a concentration of 5% of active Grignard compound is not exceeded during the reaction in the process of the invention. The alkyl Grignard is formed preferentially with high selectivity.

The handling and slow metered addition of an isolated, pyrophoric Grignard compound is no longer necessary as a result of the slow and uniform formation of the active Grignard in situ. Use of the process of the invention therefore significantly reduces the hazard potential in a large-scale, industrial process and thus considerably improves process safety.

The radical R in formula (I) or formula (II) is a substituted or unsubstituted alkenylic, cycloalkenylic, aromatic or heteroaromatic radical, where the heteroaromatic radical is a five-, six- or seven-membered ring having one or more nitrogen, oxygen and/or sulphur atoms in the ring. The cycloalkenylic, aromatic and heteroaromatic radicals may, if appropriate, have further aromatic, heteroaromatic and/or cycloaliphatic radicals fused onto them.

Examples of aromatic radicals R are phenyl, naphthyl, tolyl, anisole, cresol, aniline or benzoic acid radicals. An example of a heteroaromatic radical is pyridine radicals. Examples of alkenylic radicals R are 2-methylpropenyl and 2-phenylethenyl radicals. An example of a cycloalkenylic radical is the 1-cyclohexenyl radical.

The alkenylic, cycloalkenylic, aromatic or heteroaromatic radical R can bear up to eight substituents which can be, independently of one another, $(C_1\text{-}C_{12})$-alkyl, $(C_1\text{-}C_{12})$-cycloalkyl, $(C_1\text{-}C_{12})$-alkenyl, $(C_1\text{-}C_{12})$-cycloalkenyl, $(C_1\text{-}C_{12})$-alkynyl, $(C_1\text{-}C_{12})$-aryl, O—[$(C_1\text{-}C_{12})$-alkyl], O—[$(C_1\text{-}C_{12})$-aryl], O—Si[$(C_1\text{-}C_{12})$-alkyl]$_n$[$(C_1\text{-}C_{12})$-aryl]$_{3-n}$, OC(O)—[$(C_1\text{-}C_{12})$-alkyl], OC(O)—[$(C_1\text{-}C_{12})$-aryl], NH$_2$, NH[$(C_1\text{-}C_{12})$-alkyl], N[$(C_1\text{-}C_{12})$-alkyl]$_2$, NH[$(C_1\text{-}C_{12})$-aryl], N[$(C_1\text{-}C_{12})$-aryl]$_2$, NHC(O)—[$(C_1\text{-}C_{12})$-alkyl], N[$(C_1\text{-}C_{12})$-alkyl]C(O)—[$(C_1\text{-}C_{12})$-alkyl], NHC(O)—[$(C_1\text{-}C_{12})$-aryl], N[$(C_1\text{-}C_{12})$-alkyl]C(O)—[$(C_1\text{-}C_{12})$-aryl], NO$_2$, NO, S—[$(C_1\text{-}C_{12})$-aryl], S—[$(C_1\text{-}C_{12})$-alkyl], fluorine, chlorine, bromine, CF$_3$, CN, COOM, COO—[$(C_1\text{-}C_{12})$-alkyl], COO—[$(C_1\text{-}C_{12})$-aryl], C(O)NH—[$(C_1\text{-}C_{12})$-alkyl], C(O)NH—[$(C_1\text{-}C_{12})$-aryl], C(O)N—[$(C_1\text{-}C_{12})$-alkyl]$_2$, C(O)N—[$(C_1\text{-}C_{12})$-aryl]$_2$, CHO, SO$_2$—[$(C_1\text{-}C_{12})$-alkyl], SO—[$(C_1\text{-}C_{12})$-alkyl], SO$_2$—[$(C_1\text{-}C_{12})$-aryl], SO—[$(C_1\text{-}C_{12})$-aryl], OSO$_2$—[$(C_1\text{-}C_{12})$-alkyl], OSO$_2$—[$(C_1\text{-}C_{12})$-aryl], PO—[$(C_1\text{-}C_{12})$-alkyl]$_2$, PO—[$(C_1\text{-}C_{12})$-aryl]$_2$, SO$_3$M, SO$_3$—[$(C_1\text{-}C_{12})$-alkyl], SO$_3$—[$(C_1\text{-}C_{12})$-aryl] or Si[$(C_1\text{-}C_{12})$-alkyl]$_n$[$(C_1\text{-}C_{12})$-aryl]$_{3-n}$, where M is an alkali metal or alkaline earth metal atom and n is a natural number in the range from 0 to 3.

The alkylic, alkenylic, cycloalkylic or cycloalkenylic radical R' in formula (I) or formula (II) may, if appropriate, bear one or more substituents which can be, independently of one another, $(C_1\text{-}C_{12})$-alkyl, $(C_1\text{-}C_{12})$-cycloalkyl, $(C_1\text{-}C_{12})$-alkenyl, $(C_1\text{-}C_{12})$-cycloalkenyl, $(C_1\text{-}C_{12})$-alkynyl, $(C_1\text{-}C_{12})$-aryl, O—[$(C_1\text{-}C_{12})$-alkyl], O—[$(C_1\text{-}C_{12})$-aryl], O—Si[$(C_1\text{-}C_{12})$-alkyl]$_n$[$(C_1\text{-}C_{12})$-aryl]$_{3-n}$, OC(O)—[$(C_1\text{-}C_{12})$-alkyl], OC(O)—[$(C_1\text{-}C_{12})$-aryl], NH$_2$, NH[$(C_1\text{-}C_{12})$-alkyl], N[$(C_1\text{-}C_{12})$-alkyl]$_2$, NH[$(C_1\text{-}C_{12})$-aryl], N[$(C_1\text{-}C_{12})$-aryl]$_2$, NHC(O)—[$(C_1\text{-}C_{12})$-alkyl], N[$(C_1\text{-}C_{12})$-alkyl]C(O)—[$(C_1\text{-}C_{12})$-alkyl], NHC(O)—[$(C_1\text{-}C_{12})$-aryl], N[$(C_1\text{-}C_{12})$-alkyl]C(O)-[$C_1\text{-}C_2$)-aryl], NO$_2$, NO, S—[$(C_1\text{-}C_{12})$-aryl], S—[$(C_1\text{-}C_{12})$-alkyl], fluorine, chlorine, bromine, CF$_3$, CN, COOM, COO—[$(C_1\text{-}C_{12})$-alkyl], COO—[$(C_1\text{-}C_{12})$-aryl], C(O)NH—[$(C_1\text{-}C_{12})$-alkyl], C(O)NH—[$(C_1\text{-}C_{12})$-aryl], C(O)N—[$(C_1\text{-}C_{12})$-alkyl]$_2$, C(O)N—[$(C_1\text{-}C_{12})$-aryl]$_2$, CHO, SO$_2$—[$(C_1\text{-}C_{12})$-alkyl], SO—[$(C_1\text{-}C_{12})$-alkyl], SO$_2$—[$(C_1\text{-}C_{12})$-aryl], SO—[$(C_1\text{-}C_{12})$-aryl], OSO$_2$—[$(C_1\text{-}C_{12})$-alkyl], OSO$_2$—[$(C_1\text{-}C_{12})$-aryl], PO—[$(C_1\text{-}C_{12})$-alkyl]$_2$, PO—[$(C_1\text{-}C_{12})$-aryl]$_2$, SO$_3$M, SO$_3$—[$(C_1\text{-}C_{12})$-alkyl], SO—[$(C_1\text{-}C_{12})$-aryl] or Si[$(C_1\text{-}C_{12})$-alkyl]$_n$[$(C_1\text{-}C_{12})$-aryl]$_{3-n}$, where M is an alkali metal or alkaline earth metal atom and n is a natural number in the range from 0 to 3.

Examples of alkylic radicals R' are linear and branched, substituted or unsubstituted $C_3\text{-}C_{12}$-alkyls, an example of a cycloalkylic radical is cyclohexyl, examples of alkenylic radicals are linear and branched, substituted or unsubstituted $C_3\text{-}C_{12}$-olefins and an example of a cycloalkenylic radical is 1-cyclohexenyl.

Preference is given to using transition metal compounds of groups 7 to 12 of the Periodic Table (transition metals) as catalysts.

Further preference is given to using iron or cobalt compounds, particularly preferably iron(II) chloride, iron(III) chloride, iron(II) acetylacetonate, iron(III) acetylacetonate, iron(II) acetate, iron(III) acetate, iron(II) bromide, iron(III) bromide, iron(II) fluoride, iron(III) fluoride, iron(II) iodide, iron(III) iodide, iron(II) sulphate, iron(III) chloride-TMEDA complex, iron carbonyl complexes, cobalt(II) chloride, cobalt (III) chloride, cobalt(II) acetylacetonate, cobalt(III) acetylacetonate, cobalt(II) acetate, cobalt(III) acetate, cobalt(II) bromide, cobalt(III) bromide, cobalt(II) fluoride, cobalt(III) fluoride, cobalt(II) iodide, cobalt(III) iodide, cobalt(II) sulphate, cobalt(III) sulphate, cobalt(II) cyanide, cobalt(III) cyanide, cobalt(II) oxide, cobalt(III) oxide, cobaltcarbonyl complexes, bis(cyclopentadienyl)cobalt(II), bis (cyclopentadienyl)cobalt(III) salts, dichlorobis (ethylenediamine)cobalt(III) salts, tris(ethylenediamine)

cobalt(III) salts, chlorotris(triphenylphosphine)cobalt(I), dichlorobis(triphenylphosphine)cobalt(II), [1,1'-bis(diphenylphosphino)ferrocene]dichlorocobalt(II), (R,R)-(−)-N,N'-bis(3,5-di-tert-butylsalicylidene)-1,2-cyclohexanediaminecobalt(II), N,N'-bis(salicylidene)ethylenediaminecobalt (II) or [1,2-bis(diphenylphosphino)ethane]dichlorocobalt (II).

The amount of catalyst used is preferably from 0.01 to 50 mol %, particularly preferably from 0.1 to 10 mol %, based on the compound of the general formula (II).

If desired, additives can be added in the process of the invention (item c).

The nitrogen-, oxygen- and/or phosphorus-containing additives having one or more nitrogen, oxygen and/or phosphorus atoms which may be added are preferably substituted or unsubstituted alkylamines, N-containing heterocycles, alkylamides, cyclic alkylamides, cycloalkylamines, cycloalkyldiamines, alkylamines, cycloalkylamines, aniline, aniline derivatives, nitrogen-containing heteroaromatics, dialkyl ethers, alkylaryl ethers, diaryl ethers, cyclic ethers, oligoethers, polyethers, triarylphosphanes, trialkylphosphanes, aryldialkylphosphanes, alkyldiarylphosphanes and bridged bisphosphanes.

Particular preference is given to using TEA (triethylamine), ethyldiisopropylamine, TMEDA (N,N,N',N'-tetramethylethylenediamine), DABCO (1,4-diazabicyclo [2.2.2]octane), (−)-Spartein, N,N,N',N'-tetramethyldiaminomethane, DACH (1,2-diaminocyclohexane), Me$_4$-DACH (N,N,N',N'-tetramethyl-1,2-diaminocyclohexane), NMP (N-methyl-2-pyrrolidone), N,N-dimethylaniline, pyridine, phenanthroline, PEG (polyethylene glycol), DME (1,2-dimethoxyethane) binaphthyl dimethyl ether, 18-crown-6, triphenylphosphane, tri-n-butylphosphane, tri-tert-butylphosphane, dppf (1,1'-bis(diphenylphosphino)ferrocene), dppe (1,2-bis(diphenylphosphino) ethane), dppp (1,3-bis(diphenylphosphino)propane), dpph (1,4-bis(diphenylphosphino)butane) or dpppe (1,5-bis(diphenylphosphino)pentane as additive.

The use of chiral nitrogen-, oxygen- and/or phosphorus-containing additives having one or more nitrogen, oxygen and/or phosphorus atoms in the process of the invention leads, with suitable choice of substrates, to selective formation of an asymmetric centre of the formula (IVa) or formula (IVb) in stereoisomerically enriched form, where R is as defined for formula (I) and R1, R2 and R3 can have, independently of one another, the following meanings: hydrogen, (C$_1$-C$_{12}$)-alkyl, (C$_1$-C$_{12}$)-cycloalkyl, (C$_1$-C$_{12}$)-alkenyl, (C$_1$-C$_{12}$)-cycloalkenyl, (C$_1$-C$_{12}$)-alkynyl, (C$_1$-C$_{12}$)-aryl, O—[(C$_1$-C$_{12}$)-alkyl], O—[(C$_1$-C$_{12}$)-aryl], O—Si[((C$_1$-C$_{12}$)-alkyl]$_n$[C$_1$-C$_{12}$)-aryl]$_{3-n}$, OC(O)—[(C$_1$-C$_{12}$)-alkyl], OC(O)—[(C$_1$-C$_{12}$)-aryl], NH$_2$, NH[(C$_1$-C$_{12}$)-alkyl], N[(C$_1$-C$_{12}$)-alkyl]$_2$, NH[(C$_1$-C$_{12}$)-aryl], N[(C$_1$-C$_{12}$)-aryl]$_2$, NHC(O)—[(C$_1$-C$_{12}$)-alkyl], N[(C$_1$-C$_{12}$)-alkyl]C(O)—[(C$_1$-C$_{12}$)-alkyl], NHC(O)—[(C$_1$-C$_{12}$)-aryl], N[(C$_1$-C$_{12}$)-alkyl]C(O)—[(C$_1$-C$_{12}$)-aryl], NO$_2$, NO, S—[(C$_1$-C$_{12}$)-aryl], S—[(C$_1$-C$_{12}$)-alkyl], fluorine, chlorine, bromine, CF$_3$, CN, COOM, COO—[(C$_1$-C$_{12}$)-alkyl], COO—[(C$_1$-C$_{12}$)-aryl], C(O)NH—[(C$_1$-C$_{12}$)-alkyl], C(O)NH—[(C$_1$-C$_{12}$)-aryl], C(O)N—[(C$_1$-C$_{12}$)-alkyl]$_2$, C(O)N—[(C$_1$-C$_{12}$)-aryl]$_2$, CHO, SO$_2$—[(C$_1$-C$_{12}$)-alkyl], SO—[(C$_1$-C$_{12}$)-alkyl], SO$_2$—[(C$_1$-C$_{12}$)-aryl], SO—[(C$_1$-C$_{12}$)-aryl], OSO$_2$—[(C$_1$-C$_{12}$)-alkyl], SO$_2$—[(C$_1$-C$_{12}$)-aryl], PO—[(C$_1$-C$_{12}$)-alkyl]$_2$, PO—[(C$_1$-C$_{12}$)-aryl]$_2$, SO$_3$M, SO$_3$—[(C$_1$-C$_{12}$)-alkyl], SO$_3$—[(C$_1$-C$_{12}$)-aryl] or Si[(C$_1$-C$_{12}$)-alkyl]$_n$[(C$_1$-C$_{12}$)-aryl]$_{3-n}$, where M is an alkali metal or alkaline earth metal atom and n is a natural number in the range from 0 to 3. However, it is necessary that R≠R1≠R2≠R3, R, R1, R2 and/or R3 can, independently of one another, be bridged to one another via the abovementioned substituents. The carbon atom together with the radicals R1, R2 and R3 corresponds to R' with the meaning given for formula (I).

The formation of one or other stereoisomer in stereoisomerically enriched form is controlled in a targeted manner in the process of the invention by choice of the chiral ligand/additive.

Chiral ligands used are nitrogen-, oxygen- and/or phosphorus-containing additives having one or more nitrogen, oxygen and/or phosphorus atoms, preferably substituted or unsubstituted alkylamines, N-containing heterocycles, alkylamides, cyclic alkylamides, cycloalkylamines, cycloalkyldiamines, alkylimines, cycloalkylimines, aniline, aniline derivatives, nitrogen-containing heteroaromatics, dialkyl ethers, alkyl aryl ethers, diaryl ethers, cyclic ethers, oligoethers, polyethers, triarylphosphanes, trialkylphosphanes, aryldialkylphosphanes, alkyldiarylphosphanes and bridged bisphosphanes having one or more centres of chirality.

In the process of the invention, the nitrogen-, oxygen- and/or phosphorus-containing additive is preferably used in an amount of from 0 to 200 mol %, particularly preferably from 1 to 150 mol %, based on the compounds (II).

The process of the invention is usually carried out in aprotic polar solvents. Particular preference is given to using tetrahydrofuran (THF), 2-methyltetrahydrofuran (2-methyl-THF), 1,4-dioxane, dimethylformamide (DMF), dimethylacetamide (DMAc), methyl tert-butyl ether (MTBE), diethyl ether, 1,2-dimethoxyethane (DME), diisopropyl ether (DIPE), dimethyl carbonate or N-methyl-2-pyrrolidone (NMP) as solvent.

The reaction temperature in the process of the invention is usually in the range from −80° C. to +100° C.

The process of the invention allows reaction of many substituted and unsubstituted aryl-X, heteroaryl-X, cycloalkenyl-X and alkenyl-X compounds, where X is a leaving group such as halide, diazonium, mesylate, tosylate or triflate, with substituted and unsubstituted alkyl, alkenyl, cycloalkyl or cycloalkenyl halides to form the corresponding functionalized aromatics, heteroaromatics and olefins.

The compounds prepared by the process of the invention can readily be isolated and purified by conventional methods.

The process of the invention is very suitable for generating centres of chirality in a targeted and selective manner by means of cross-coupling.

EXAMPLES

Examples 1 to 15

At a temperature of 0° C., 29 mg (1.2 mmol) of magnesium turnings are placed in a 10 ml reaction flask and flushed with argon. A solution comprising 8.1 mg of FeCl$_3$ (0.005 mmol; 5 mol %) and 4 ml of THF (anhydrous) is added and 181 μl of TMEDA (1.2 mmol) are subsequently introduced. The mixture is stirred at a temperature of 0° C. for 30 minutes and the compound R—X (1 mmol) and the compound R'—Y (1.2 mmol) are then added. The reaction mixture is stirred at room temperature for 3 hours and the reaction is subsequently stopped by addition of 3 ml of a saturated aqueous ammonium chloride solution and 1 ml of 10% strength aqueous HCl. The mixture is extracted with 3×5 ml of ethyl acetate, the combined organic phases are dried over sodium sulphate and the solvent is distilled off under reduced pressure. The crude product is purified by column chromatography (silica gel, cyclohexane, ethyl acetate).

$$R-X + Y-R' \xrightarrow[\text{THF}]{\text{FeCl}_3, \text{TMEDA}} R-R'$$

| Example | R—X | R'—Y | R—R' | Yield |
|---|---|---|---|---|
| 1 | bromobenzene | bromocyclohexane | cyclohexylbenzene | 77% |
| 2 | 1-bromonaphthalene | 1-bromopentane | 1-pentylnaphthalene | 71% |
| 3 | 1-bromonaphthalene | 1-bromododecane | 1-dodecylnaphthalene | 75% |
| 4 | 1-bromonaphthalene | bromocyclohexane | 1-cyclohexylnaphthalene | 67% |
| 5 | 4-bromotoluene | bromocyclohexane | 4-cyclohexyltoluene | 77% |
| 6 | 4-bromotoluene | 2-bromobutane | 4-(sec-butyl)toluene | 62% |
| 7 | 4-bromotoluene | 6-bromo-1-hexene | 4-(hex-5-en-1-yl)toluene | 55% |

-continued $$R\text{—}X \quad + \quad Y\text{—}R' \quad \xrightarrow[\text{THF}]{\substack{\text{FeCl}_3 \\ \text{TMEDA}}} \quad R\text{—}R'$$

| Example | R—X | R'—Y | R—R' | Yield |
|---|---|---|---|---|
| 8 | 4-Br-C₆H₄-CH₃ | Br-(CH₂)₄-C(O)-OtBu | 4-CH₃-C₆H₄-(CH₂)₅-C(O)-OtBu | 40% |
| 9 | 4-tBu-C₆H₄-Br | Br-CH₂-CH(CH₃)₂ | 4-tBu-C₆H₄-CH₂-CH(CH₃)₂ | 67% |
| 10 | 4-MeO-C₆H₄-Br | cyclohexyl-Br | 4-MeO-C₆H₄-cyclohexyl | 65% |
| 11 | 2-MeO-C₆H₄-Br | Br-(CH₂)₃-Ph | 2-MeO-C₆H₄-(CH₂)₃-Ph | 74% |
| 12 | 2-MeO-C₆H₄-Br | cyclohexyl-Br | 2-MeO-C₆H₄-cyclohexyl | 69% |
| 13 | 4-Me₂N-C₆H₄-Br | cyclohexyl-Br | 4-Me₂N-C₆H₄-cyclohexyl | 75% |
| 14 | ethyl 2-bromobenzoate | Br-(CH₂)₁₁-CH₃ | ethyl 2-(dodecyl)benzoate | 40% |
| 15 | 2-Br-pyridine | cyclohexyl-Br | 2-cyclohexylpyridine | 55% |

Examples 16 to 20

Using a procedure similar to Examples 1-15, aryl and alkyl chlorides and aryl triflates were also able to be employed successfully. In the case of phenyl triflate (phenyl trifluoromethanesulphonate) and chlorobenzene, the reaction was carried out at 20° C.

| Example | R—X | R'—Y | R—R' | Yield |
|---|---|---|---|---|
| 16 | phenyl chloride | cyclohexyl bromide | cyclohexylbenzene | 20% |
| 17 | phenyl bromide | cyclohexyl chloride | cyclohexylbenzene | 25% |
| 18 | 2-bromoanisole | cyclohexyl chloride | 2-cyclohexylanisole | 39% |
| 19 | 2-chloropyridine | cyclohexyl bromide | 2-cyclohexylpyridine | 30% |
| 20 | phenyl triflate (OSO$_2$CF$_3$) | 1-bromopropane | propylbenzene | 80% |

Example 21

Using a procedure similar to Examples 1-15, alkenyl bromides are also able to be reacted successfully with alkyl bromides.

| Example | R—X | R'—Y | R—R' | Yield |
|---|---|---|---|---|
| 21 | 2-methyl-1-bromopropene | 3-phenylpropyl bromide | 6-methyl-1-phenyl-5-heptene | 48% |

Example 22

Using a procedure similar to Examples 1-15 but using 10 mol % of TMEDA instead of 120 mol %, 4-bromotoluene is able to be reacted successfully with 1-bromododecane.

| Example | R—X | R'—Y | R—R' | Yield |
|---|---|---|---|---|
| 22 | 4-BrC₆H₄CH₃ | Br(CH₂)₁₀CH₃ | 4-CH₃C₆H₄(CH₂)₁₀CH₃ | 53% |

Examples 23 to 31

Using a procedure similar to Examples 1-15, 4-bromoanisole was reacted with 1-bromododecane. Electronically and sterically different nitrogen-containing additives were used instead of TMEDA.

MeO-C₆H₄-Br + Br-(CH₂)₁₀-CH₃ →(5 mol % FeCl₃, amine, 1.1 equiv. Mg, THF, 20° C.) MeO-C₆H₄-(CH₂)₁₀-CH₃

| Example | Additive | Yield |
|---|---|---|
| 23 | 1,10-Phenanthroline | 63% |
| 24 | Pyridine | 72% |
| 25 | N,N-Dimethylaniline | 49% |
| 26 | N-Methylpyrrolidone | 39% |
| 27 | Tetramethyldiaminomethane | 72% |
| 28 | Ethyldiisopropylamine | 44% |
| 29 | TMEDA | 77% |
| 30 | (−)-Spartein | 36% |
| 31 | DABCO | 75% |

Examples 32 to 35

In a manner analogous to Examples 23-31, oxygen- and phosphorus-containing compounds such as ethers and phosphanes are also suitable as additives in the cross-coupling of 4-bromoanisole and 1-bromododecane. As Example 32 shows, the reaction also proceeds successfully in the absence of any additives.

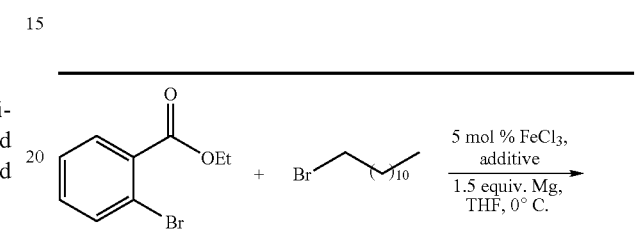

| Example | Additive | mol % | Yield |
|---|---|---|---|
| 32 | — | — | 30% |
| 33 | (2,2'-dimethoxy-1,1'-binaphthyl) | 20 | 73% |
| 34 | 18-crown-6 | 20 | 55% |
| 35 | PPh₃ | 20 | 51 |

Examples 36 to 44

At room temperature 29 mg (1.2 mmol) of magnesium turnings are placed in a 10 ml reaction flask and flushed with argon. A solution comprising 6.5 mg of CoCl₂ (0.05 mmol; 5 mol %) and 4 ml of THF (anhydrous) is added and 19 μl of N,N,N',N'-tetramethyl-1,2-diaminocyclohexane (Me4DACH; 0.11 mmol, 11 mol %) are subsequently introduced. The blue mixture is cooled to a temperature of 0° C. while stirring and the compound R—X (1.0 mmol) and the compound R'—Y (1.0 mmol) are then added. The reaction mixture is stirred at 0° C. for 3 hours and the reaction is subsequently stopped by addition of 3 ml of a saturated aqueous ammonium chloride solution. The mixture is extracted with 3×5 ml of ethyl acetate, the combined organic phases are dried over sodium sulphate and the solvent is distilled off under reduced pressure. The crude product is purified by column chromatography (silica gel, cyclohexane, ethyl acetate).

| Example | R—X | R'—Y | R—R' | Yield |
|---|---|---|---|---|
| 36 | 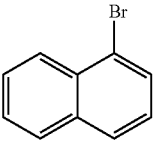 | 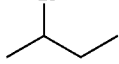 | 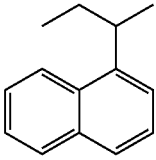 | 64% |
| 37 | 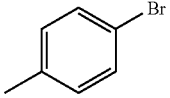 | 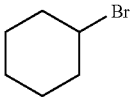 | 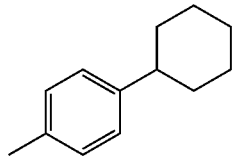 | 67% |
| 38 | 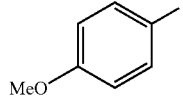 | 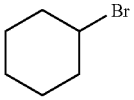 | 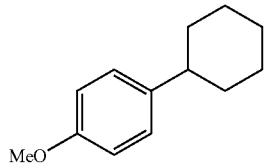 | 52% |
| 39 | 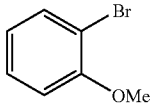 | 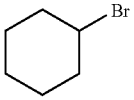 | 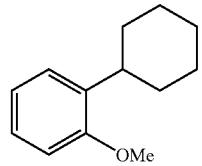 | 60% |
| 40 | 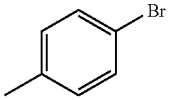 | 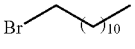 | 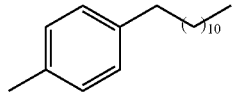 | 66% |
| 41 | 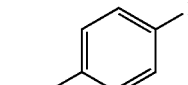 | 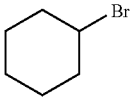 | 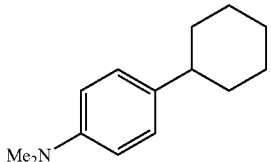 | 42% |
| 42 | 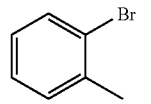 | 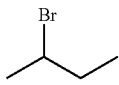 | 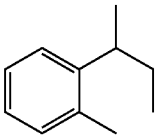 | 52% |
| 43 | 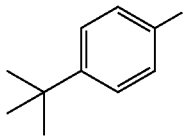 | 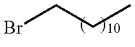 | 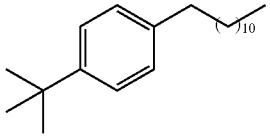 | 53% |
| 44 | 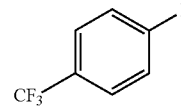 | 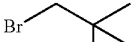 | 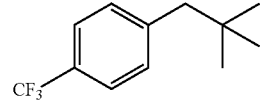 | 46% |
Reaction conditions: R—X + Y—R' → R—R' (CoCl$_2$, Me$_4$DACH, THF)

Examples 45 to 47

Using a procedure similar to Examples 36-44, aryl and alkyl chlorides can also be used successfully.

| Example | R—X | R'—Y | R—R' | Yield |
|---|---|---|---|---|
| 45 | 4-chlorotoluene | cyclohexyl bromide | 4-cyclohexyltoluene | 8% |
| 46 | 4-bromotoluene | cyclohexyl chloride | 4-cyclohexyltoluene | 42% |
| 47 | 4-bromotoluene | Cl—(CH₂)₁₀—CH₃ (1-chloroundecane) | 4-undecyltoluene | 7% |

Example 48

Using a procedure similar to Examples 36-44, alkenyl bromides can also be reacted successfully with alkyl bromides.

| Example | R—X | R'—Y | R—R' | Yield |
|---|---|---|---|---|
| 48 | (E)-β-bromostyrene | cyclohexyl bromide | (E)-β-cyclohexylstyrene | 35% |

Example 49

Using a procedure similar to Examples 36-44, aryl bromides can also be reacted successfully with alkenyl bromides.

| Yield | R—X | R'—Y | R—R' | Yield |
|---|---|---|---|---|
| 49 | bromobenzene | (E)-β-bromostyrene | (E)-stilbene | 19% |

Examples 50 to 55

Using a procedure similar to Examples 36-44, 4-bromotoluene was reacted with bromocyclohexane. Electronically and sterically different nitrogen-containing additives were used instead of N,N,N',N'-tetramethyl-1,2-diaminocyclohexane (Me₄DACH).

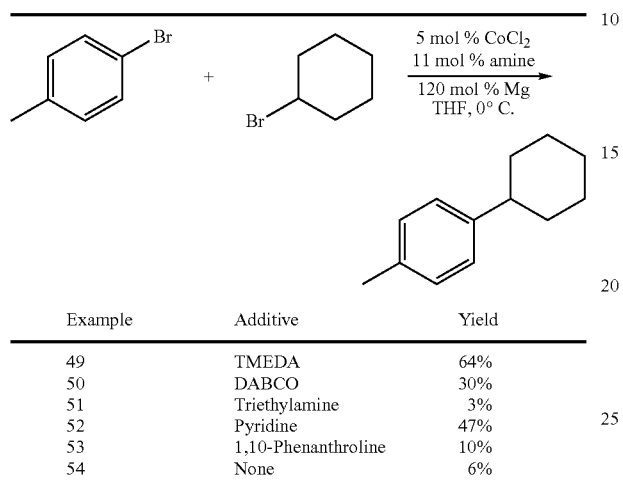

| Example | Additive | Yield |
|---|---|---|
| 49 | TMEDA | 64% |
| 50 | DABCO | 30% |
| 51 | Triethylamine | 3% |
| 52 | Pyridine | 47% |
| 53 | 1,10-Phenanthroline | 10% |
| 54 | None | 6% |

Example 53

Using a procedure similar to Examples 36-44, 2-bromoanisole was reacted with (3-bromobutyl)benzene. Instead of N,N,N',N'-tetramethyl-1,2-diaminocyclohexane (Me₄DACH) in racemic form, the optically pure 1R,2R form was used. This enabled 2-(1-methyl-3-phenyl)propylanisole to be synthesized in stereoisomerically enriched form.

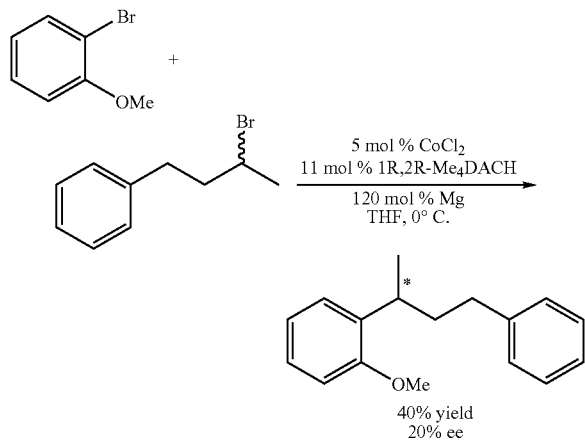

40% yield
20% ee

The invention claimed is:

1. Process for preparing organic compounds of the general formula (I)

$$R—R' \qquad (I),$$

where
R is a substituted or unsubstituted aromatic radical selected from the group consisting of phenyl, naphtyl, tolyl, anisole, cresol, aniline, and benzoic acid, and
R' is a linear, branched, substituted or unsubstitued $C_3$-$C_{12}$-alkyl radical,
by reacting a corresponding compound of the general formula (II)

$$R—X \qquad (II),$$

where
X is chlorine, bromine, iodine, diazonium, mesylate (methanesulphonate), tosylate (p-toluenesulphonate) or triflate (trifluoromethanesulphonate) and
R is as defined for formula (I),
with a corresponding compound of the general formula (III)

$$R'—Y \qquad (III),$$

where
Y is chlorine, bromine or iodine and
R' is as defined for formula (I),
wherein the reaction is carried out in the presence of
a) stoichiometric amounts of elemental magnesium, based on the compound of the general formula (II), and
b) amounts of an iron or cobalt compound from 0.01 to 50 mole percent of, based on the compound of the general formula (II),
and,
c) in the presence of a nitrogen-, oxygen- and/or phosphorus-containing additive in a catalytic or stoichiometric amount of from 0 to 200 mole percent, based on the compound of the general formula (II), and
wherein the reaction is carried out as a one-pot process in which the organomagnesium compound (Grignard compound) formed in situ as intermediate is not isolated.

2. Process according to claim 1, wherein iron(II) chloride, iron(III) chloride, iron(II) acetylacetonate, iron(III) acetylacetonate, iron(II) acetate, iron(III) acetate, iron(II) bromide, iron(III) bromide, iron(II) fluoride, iron(III) fluoride, iron(II) iodide, iron(III) iodide, iron(II) sulphate, iron(III) chloride-TMEDA complex or iron carbonyl complexes is/are used as iron compound.

3. Process according to claim 1, wherein cobalt(II) chloride, cobalt(III) chloride, cobalt(II) acetylacetonate, cobalt(III) acetylacetonate, cobalt(II) acetate, cobalt(III) acetate, cobalt(II) bromide, cobalt(III) bromide, cobalt(II) fluoride, cobalt(III) fluoride, cobalt(II) iodide, cobalt(III) iodide, cobalt(II) sulphate, cobalt(III) sulphate, cobalt(II) cyanide, cobalt(III) cyanide, cobalt(II) oxide, cobalt(III) oxide, cobaltcarbonyl complexes, bis(cyclopentadienyl)cobalt(II), bis(cyclopentadienyl)cobalt(III) salts, dichlorobis(ethylenediamine)cobalt(III) salts, tris(ethylenediamine)cobalt(III) salts, chlorotris(triphenylphosphine)cobalt(I), dichlorobis(triphenylphosphine)cobalt(II), [1,1'-bis(diphenylphosphino)ferrocene]dichlorocobalt(II), (R,R)-(−)-N,N"-bis(3,5-di-tert-butylsalicylidene)-1,2-cyclohexanediaminecobalt(II), N,N'-bis(salicylidene)ethylenediaminecobalt(II) or [1,2-bis(diphenylphosphino)ethane]dichlorocobalt(II) is used as cobalt compound.

4. Process according to claim 1, wherein substituted or unsubstituted alkylamines, N-containing heterocycles, alkylamides, cyclic alkylamides, cycloalkylamines, cycloalkyldiamines, alkylimines, cycloalkylimines, aniline, aniline derivatives, nitrogen-containing heteroaromatics, dialkyl ethers, alkyl aryl ethers, diaryl ethers, cyclic ethers, oligoethers, polyethers, triarylphosphanes, trialkylphosphanes, aryldialkylphosphanes, alkyldiarylphosphanes and bridged bisphosphanes are used as a nitrogen-, oxygen- and/or phosphorus-containing additive having one or more nitrogen, oxygen and/or phosphorus atoms which may be added.

* * * * *